Nov. 14, 1967 P. ECKE Plant Pat. 2,778
POINSETTIA PLANT
Filed June 27, 1966
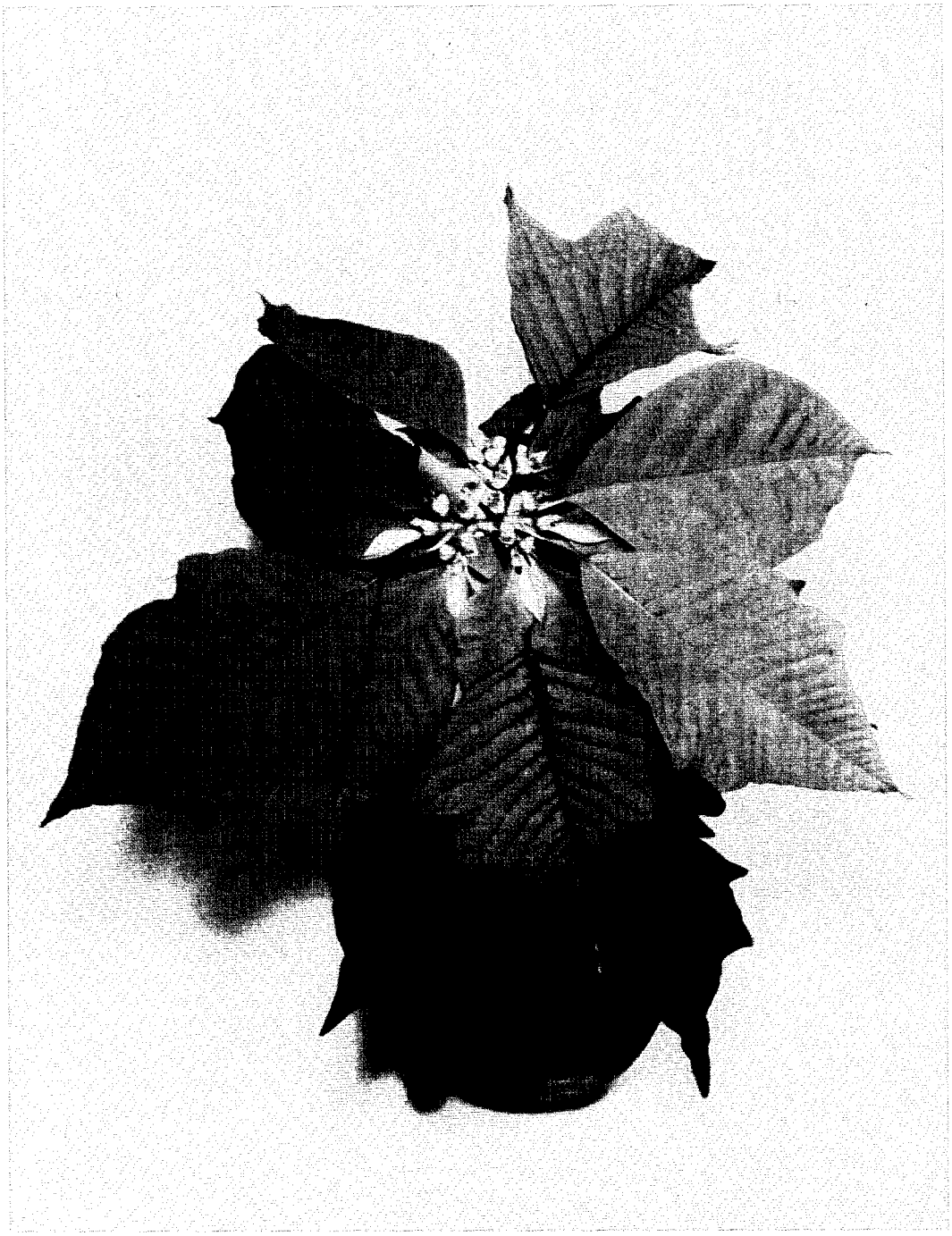
INVENTOR
PAUL ECKE
BY Wm. S. Graham
ATTORNEY United States Patent Office Plant Pat. 2,778
Patented Nov. 14, 1967

2,778
POINSETTIA PLANT

Paul Ecke, P.O. Box 488, Encinitas, Calif. 92024

Filed June 27, 1966, Ser. No. 560,986
1 Claim. (Cl. Plt.—86)

The invention disclosed herein relates to a new and distinctive variety of poinsettia plant (more specifically known botanically as *Euphorbia pulcherrima*), which was originated by me as a hybrid seedling from selective cross-pollenization to combine, control and reproduce the advantages of two selected poinsettia plants.

Broadly, this new variety of poinsettia plant is distinguishable from its parent plants as well as from other known varieties of poinsettia plants, mainly in the outstanding desirable features which may be briefly stated as follows:

(1) The vivid, intense, scintillating, dark red crimson color of the bracts.

(2) The physical formation of the involucre of bracts.

(3) The unusually long life of the bracts, inflorescence, and foliage leaves, and the tenacity thereof to adhere to the peduncle.

(4) The prominent venation of the bracts and foliage leaves.

(5) The relatively short structure of the mature plant, classifying it as semi-dwarf.

(6) The late-blooming characteristic which eliminates necessity for light treatment to delay development of bracts and inflorescence.

(7) An exceptionally vigorous and extensive root structure.

(8) A relatively short, stiff peduncle which requires no staking and provides closely spaced internodes of the foliage leaves.

(9) A luxurious inflorescence with relatively widely spaced cyathia which reasonably fill the center opening formed by petioles of the bracts.

The accompanying illustration forming a part of this specification, graphically shows this new variety in color at full maturity or optimum, the illustration being a face view of the subject plant from an elevated position, and in which some of the characteristics are shown which differentiate this new variety.

The colors referred to herein correspond approximately with the colors shown in "Dictionary of Color" by Maerz and Paul, (first edition, 1930), and identified by the commonly used color name, and by the plate of said color standard in the recapitulation in tabular form herein.

The following is a more detailed description of this new variety of poinsettia plant:

*Parentage*

This new variety of poinsettia plant was originated by me as a hybrid seedling by selective hybridization of two varieties of poinsettia plants having desirable known selective properties, the seed parent being an unnamed, unpatented seedling of a variety well known in this floricultural industry as Indianapolis Red. The pollen parent is known in the trade as Ecke White, which is unpatented, but which in turn was a sport-parent of white variety of Ecke Patent No. 1,802, dated Jan. 20, 1959. Both the Indianapolis Red and the Ecke White poinsettia plants are well known in the trade and referred to in botanical literature by those names.

*Propagation*

This new variety of poinsettia plant was developed by me by the aforesaid hybridization in a cultivated area of a glasshouse or greenhouse at my experimental and growing gardens at Encinitas, Calif. It has been asexually reproduced and cultivated by me at my said experimental gardens, by cuttings, and successive asexual reproductions thereof by such cuttings have remained true to type and to the herein described characteristics, through the propagation, cultivation and asexual reproduction thereof through several generations. Successive generations have shown its qualities and characteristics as herein set forth to be permanently fixed.

For the late fall and Christmas maturity season, such asexual propagation is preferably accomplished by slipping cuttings in July, August and early September. The slips root reasonably fast and within about 20 days the cuttings are well rooted and can be transferred to individual pots. In 60 to 75 days thereafter (a total of approximately 80 to 100 days from planting cuttings), the bracts, inflorescence, and foliage leave should reach an optimum of plant growth. The specifications of propagation exemplified herein are for optimum growth and production of bracts in the late fall and Christmas season, and assuming greenhouse cultivation, where temperatures are maintained around 60 to 75 degrees. This new variety is characterized as a naturally late bloomer since it matures its bracts and inflorescence to optimum ten to fifteen days later than such varieties as Barbara Ecke Supreme, (Plant Patent No. 1,055, dated Dec. 18, 1951), and thus requires no lighting control to delay flower bud set, which is a decided commercial advantage for the Christmas market.

It may be here noted however, that with greenhouse propagation which may be controlled as to light, temperature, fertilizers, environment, and chemical controls, planting of slips may be successfully done and optimum achieved at almost any time of year.

*Structure of plant*

This new variety roots only reasonably fast, but after rooting it has an exceptionally strong, vigorous, and extensive root system. It is naturally short in structure, at an average of 15 inches in height of peduncle from ground level to bract involucre, and requires no application of chemical growth regulator to establish its semi-dwarf structure. It does not have a rapid growth, and such delay of growth-time brings it to an optimum for the Christmas trade due to its semi-dwarf height at maturity. The peduncle is strong and stiff and requires no staking. It thus stands erect by itself and amply supports the weight of the bract involucre, which is a substantial advantage in an outdoor plant, since stakes or an artificial crutch spoils the ocular effect of the beauty of an indoor plant.

The structure of the bracts, inflorescence, and foliage leaves is more appropriately described under those headings, since they are the predominating element of novelty in this new variety.

*Bracts*

At the free axial end of the peduncle there grows an involucre of bracts on petioles which are relatively short in comparison with the length and width of the majority of bracts, thus measurably resembling the central opening of the involucre of bracts in Ecke Plant Patent No. 1,780, dated Dec. 9, 1958, though the bracts in this new variety are fewer in number. The majority of bracts are, however, very large in planar size both longitudinally and laterally, substantially equal in size to the large bracts of the aforesaid variety known as Barbara Ecke Supreme. The bracts are not numerically prolific, but because of their large planar area, they are imbricated at adjacent edges and form an unbroken wreath around the inflorescence. The bracts have a flexibility making them less liable to bruising in handling and shipping. The color of the bracts is a deep rich crimson red slightly rose tinted, and having a very vivid deep scintillating richness of color tone, closely bordering on cerise.

In shape the bracts are irregular, lacking uniformity in size and shape, being shaped in outline, partly oakleaf, and partly modified oakleaf at free terminal end and prolate at the base end, while other bracts may be generally oblate, but acuminate at the free end. Nor do all the bracts lie in the same general plane, the planes of some separate individual bracts being at angular inclination to other bracts, which, in side elevation provides unusual thickness of red coloring to the involucre and thereby emphasizes the vivid dynamic crimson color.

Further distinctive characteristics of the bracts are their prominent herring-bone venation; and the majority of bracts have a double convexity from the main center vein to the outer margin of the bracts, resembling the double arc of a gull's wings in gliding flight.

The bracts are also very long lasting, as is also characteristic of the foliage leaves and the inflorescence, similar to the lasting qualities of the pollen patent, Eske White, frequently lasting at optimum of bracts and inflorescence for as much as four weeks, given normal care of water and moderate temperatures.

*Inflorescence*

In the center of the bract involucre is an open space formed by the length of petioles of the bracts. In this new variety this center opening is not excessively large due to the relative short petioles of the bracts. From the free terminal axial end of the peduncle, several light green spurs sprout into the central opening. Upon these spurs are formed the sub-acaulescant inflorescence which is plentiful and well spaced to substantially fill such central opening of the bract involucre. As part of the inflorescence there usually are also a few very small ancillary leaflets of a yellow color radiating from the spurs. There is nothing unusual about the flower coloring. The cyathia are pale green, the flower cups are orange-yellow, and the center portion of the flower, whether stamen, stigma or pistil, are a crimson red substantially similar to the color of the bracts.

*Foliage leaves*

The foliage leaves of this new variety are arranged around the peduncle, the nodes thereof being quite uniformly spaced and reasonably close together, averaging approximately 3 inches apart in the nature of a helix. Their spacing however, is somewhat dependent on the rapidity of growth of the plant. Like the bracts, the foliage leaves hold tenaciously to the peduncle and in shape they vary in peripheral outline, some being oakleaf, others shield shape, others oblate toward the base, and acuminate at the free terminal end. The venation of the foliage leaves is herring-bone type and quite distinctly apparent. Those foliage leaves which are spaced remotely from the bracts are dark ivy green in color, whereas those closely adjacent to the bracts are generally tinted a brownish-red with lines of dark green following the venation.

*Immunity*

This new variety is hardy and healthy in growth, though its rate of growth may be characterized as slow, resulting in its semi-dwarf height at maturity. It seems to have an unusual resistance to some of the diseases which frequently are present in poinsettia plants. More particularly, this new variety is unusually resistant to a stem rot disease condition which is usually recognized as being caused by a root fungus designated rhizoctonia, and is also unusually resistant to a root rot condition caused by a fungus thielaviopsis, the detrimental factors of which are principally evidenced by leaf-drop of the foliage prior to complete maturity of the bract involucre and inflorescence. This resistance to disease has been observed in this new variety when it has been grown side-by-side with other existing known varieties under the same soil, temperature and moisture conditions at Encinitas, Calif.

*Variations*

Individual plants of this new variety have an unusual similarity, and successive asexually reproduced generations exhibit an adherence to characteristics and type herein described. However, there may be some variation in the characteristics of minor details, in the comparison of plants grown in different localities, in different soils, at different times of the year, varying temperatures, varying types of glass-house, or out-of-doors, or because of treatment with light or chemicals. The conditions set forth herein are especially pertinent and prevalent in conditions of propagation and cultivation at my experimental gardens at Encinitas, which is in southern California, where, in field conditions, the night-time temperatures frequently go down into the lower forties F., whereas with plants growing in a greenhouse, the temperature is preferably maintained practically uniform around 60 to 75 degrees F.

*Color tabulation*

The color designations according to the color plates of the aforesaid "Dictionary of Color" are recapitulated in tabular form as follows:

| Part of Plant | Non-Technical Designation of Color | Dictionary of Color | | |
|---|---|---|---|---|
| | | Plate | Letter | Number |
| Peduncle | Greenish-brown | 8 | L | 6 |
| Bracts | Deep rich crimson red, faintly rose tinted, bordering on cerise. | 4 | L | 6 |
| Foliage leaves: | | | | |
| (a) Remote from bracts. | Dark ivy green | 32 | L | 1 |
| (b) Adjacent to bracts | Partially or wholly brownish-red tinged by dark greenish venation. | 6 | L | 6 |
| Inflorescence: | | | | |
| (a) Cyathium | Pale green | 20 | E | 4 |
| (b) Flower | Orange yellow | 10 | L | 7 |
| (c) Center portion | Crimson red faintly rose tinted. | 4 | J | 6 |
| (d) Ancillary leaflets of inflorescence. | Pale yellow | 10 | H | 5 |
| (e) Spurs mounting flowers and ancillary leaflets. | Pale green | 40 | E | 4 |

Having described and illustrated my new variety of poinsettia plant, I claim:

A new and distinct variety of poinsettia plant as illustrated and described, and more particularly characterized by its relatively short height, and essentially by an involucre of bracts which have a deep rich crimson red color faintly tinted with rose bordering on cerise, the bracts being relatively few numerically and unusually large both in length and width, and forming a generally planar wreath of bracts imbricated at adjacent edges, the bracts and foliage leaves having clearly defined venation; said bracts being of varying shapes, and a portion of such bracts being irregularly arranged out of the general plane of the involucre of the bracts; the plant having a large, vigorous root structure, and a short, stiff peduncle requiring no staking support for the mature plant; coupled with naturally late blooming characteristics requiring no treatment with lights to delay optimum development of growth of bracts and inflorescence for the Christmas market, together with exceptionally long-lasting qualities of maintaining an optimum of appearance of bracts, inflorescence and foliage leaves over an exceptionally long period of time.

No references cited.

ROBERT E. BAGWILL, *Primary Examiner.*